(12) United States Patent
Singh et al.

(10) Patent No.: US 9,988,398 B2
(45) Date of Patent: Jun. 5, 2018

(54) CRYSTALLINE FORM OF RIFAXIMIN AND PROCESS FOR ITS PREPARATION

(71) Applicant: CADILA HEALTHCARE LIMITED, Ahmedabad, Gujarat (IN)

(72) Inventors: Kumar Kamlesh Singh, Ahmedabad-Gujarat (IN); Nikhil Amar Singh, Ahmedabad-Gujarat (IN); Prashant Rameshchandra Bhatt, Ahmedabad-Gujarat (IN); Amol Kashinath Patil, Ahmedabad-Gujarat (IN)

(73) Assignee: CADILA HEALTHCARE LIMITED, Ahmedabad (IN)

( * ) Notice: Subject to any disclaimer, the term of this patent is extended or adjusted under 35 U.S.C. 154(b) by 0 days. days.

(21) Appl. No.: 15/614,900

(22) Filed: Jun. 6, 2017

(65) Prior Publication Data

US 2017/0349608 A1    Dec. 7, 2017

(30) Foreign Application Priority Data

Jun. 7, 2016 (IN) .............................. 201621019542

(51) Int. Cl.
  *C07D 491/22* (2006.01)
  *A61K 31/395* (2006.01)
  *C07D 498/22* (2006.01)

(52) U.S. Cl.
  CPC .......... *C07D 498/22* (2013.01); *A61K 31/395* (2013.01); *C07D 491/22* (2013.01); *C07B 2200/13* (2013.01)

(58) Field of Classification Search
  CPC ........................... C07D 491/22; A61K 31/395
  USPC .......................................... 540/456; 514/279
  See application file for complete search history.

(56) References Cited

U.S. PATENT DOCUMENTS

| | | | |
|---|---|---|---|
| 4,341,785 A | 7/1982 | Marchi et al. | |
| 4,557,866 A | 12/1985 | Cannata et al. | |
| 7,045,620 B2* | 5/2006 | Viscomi ............... | C07D 498/22 540/456 |
| 7,709,634 B2 | 5/2010 | Kothakonda et al. | |
| 8,067,429 B2 | 11/2011 | Gushurst et al. | |
| 8,193,196 B2 | 6/2012 | Viscomi et al. | |
| 8,633,234 B2 | 1/2014 | Rao et al. | |

FOREIGN PATENT DOCUMENTS

| | | |
|---|---|---|
| IT | 1154655 B | 1/1987 |
| WO | 2013/027227 A1 | 2/2013 |
| WO | 2015/159275 A2 | 10/2015 |

OTHER PUBLICATIONS

Viscomi, G. C., et al., "Chrystal forms of rifaximin and their effect on pharmaceutical properties", CrystEngComm, 2008, vol. 10, pp. 1074-1081.

\* cited by examiner

*Primary Examiner* — Venkataraman Balasubramanian
(74) *Attorney, Agent, or Firm* — Ladas & Parry LLP

(57) ABSTRACT

A novel crystalline form of rifaximin and process for its preparation are described. A pharmaceutical composition comprising crystalline rifaximin is also described.

10 Claims, 3 Drawing Sheets

CRYSTALLINE FORM OF RIFAXIMIN AND PROCESS FOR ITS PREPARATION

FIELD OF THE INVENTION

The present invention relates a novel crystalline form of rifaximin and process for its preparation. In particular, the present invention relates to a process for preparing crystalline rifaximin. More particularly, the present invention relates to a pharmaceutical composition comprising crystalline rifaximin.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Rifaximin of Formula I, is an antibiotic belonging to rifamycin class of antibiotics and is chemically known as (2S,16Z,18E,20S,21S,22R,23R,24R,25S,26S,27S, 28E)-5,6,21,23,25-pentahydroxy-27-methoxy-2,4,11,16,20,22,24,26-octamethyl-2,7-(epoxypentadeca-[1,11,13]trienimino)benzofuro[4,5-e]pyrido[1,2-a]-benzimidazole-1,15(2H)-dione, 25-acetate.

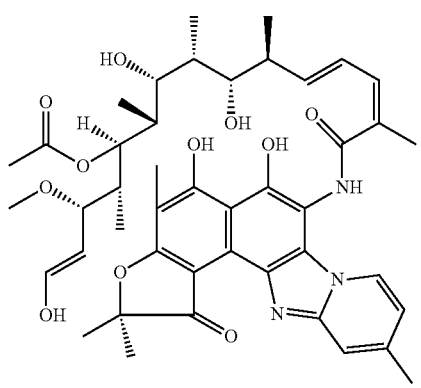

(I)

Rifaxitnin is an antibiotic pertaining to the rifamycin class, specifically it is a pyrido-imdazo rifamycin which is described in Italian patent IT 1154655. U.S. U.S. Pat. Nos. 4,341,785 and 4,557,866 disclose a process for the preparation of rifaximin starting from rifamycin S or O. The above patents describe purification steps of rifaximin by performing crystallization of crude rifaximin from a 7:3 mixture of ethyl alcohol/water and drying under atmospheric pressure and vacuum. These patents do not disclose the exact crystallization and drying conditions as well as any characterization data for confirmation on polymorphic forms of rifaximin.

U.S. Pat. No. 7,045,620 discloses three polymorphic forms α, β and γ of rifaximin. Form α and β show pure crystalline characteristics while the γ form is poorly crystalline. The US '620 discloses that the formation of the α, β and γ forms depends on the presence of water within the crystallization solvent, on the temperature at which the product is crystallized and on the amount of water present into the product at the end of the drying phase.

The polymorphic forms α, β and γ are characterized on the basis of water content and XRPD. This patent also discloses processes for preparation of these polymorphs which involve use of specific reaction conditions during crystallization like dissolving rifaximin in ethyl alcohol at 45 to 65° C., precipitation by adding water to form a suspension, filtering suspension and washing the resulted solid with water, followed by drying at room temperature under vacuum for a period of time between 2 and 72 hours. The purely crystalline forms α and β are obtained by immediate filtration of suspension when temperature of reaction mixture is brought finally to 0° C. whereas in order to obtain the poorly crystalline form γ, the reaction mixture is stirred for 5-6 hours after temperature is set to 0° C. and then filtered the suspension. The α form has water content lower than 4.5%, for β form it should be higher than 4.5% and to obtain γ form, water content should be below 2%.

CystEngComm reference article Vol. 10, Pg. 1074-1081 (2008) discloses five crystal forms of rifaximin and their effect on pharmaceutical properties. Five distinct crystal forms of rifaximin (α, β, γ, δ and ε) have been identified and characterized by X-ray powder diffraction, solid state 13C NMR, and HATR-IR spectroscopy.

U.S. Pat. No. 7,709,634 discloses an amorphous form of rifaximin and the process for the preparation thereof.

U.S. Pat. No. 8,193,196 B2 discloses polymorphic forms δ and ε of rifaximin and methods of their preparation by dissolving rifaximin in ethyl alcohol at 45 to 65° C., precipitation by adding water to form a suspension, filtering the suspension and washing the resulted solid with demineralized water, followed by drying for a period of time between 2 and 72 hours until a water content in the range 2.5-6% is obtained.

U.S. Pat. No. 7,709,634 B2 discloses amorphous form of rifaximin characterized by x-ray powder diffraction pattern as shown in FIG. 1.

U.S. Pat. No. 8,633,234 B2 discloses amorphous form of rifaximin characterized by x-ray powder diffraction pattern as shown in FIG. 1.

U.S. Pat. No. 8,067,429 B2 discloses several polymorphic forms of rifaximin such as ζ, form η, form-i, form ι-dry, form i-dry', form B, amorphous form and form Θ. Main differentiating point of these polymorphs is respective water content and x-ray powder diffraction pattern.

International PCT Publication No. WO 2013/027227 A1 discloses crystalline Form-I of rifaximin and process for its preparation.

International PCT Publication No. WO 2015/159275 A2 discloses crystalline Form G of rifaximin and process for its preparation.

It is evident from above, that rifaximin can exist in number of polymorphic forms, formation of these polymorphic forms depends upon specific reaction conditions applied during crystallization and drying. In recent times, the solid-state properties of drugs have received great attention as a major contributing factor to both bio-availability and formulation characteristics in the pharmaceutical industry. While polymorphs have the same chemical composition, they differ in packing and geometrical arrangement thereof and exhibit different physical properties such as melting point, shape, particle size, X-ray diffraction pattern, infrared absorption, and solid state NMR spectrum, density, hardness, stability, and dissolution. Depending on their temperature-stability relationship, one crystalline form may give rise to thermal behavior different from that of another crystalline form. Thermal behavior can be measured in the laboratory by techniques such as capillary melting point, thermogravimetric analysis ("TGA"), and differential scanning calorimetry ("DSC"), which have been used to distinguish polymorphic forms.

Other examples are known, where different crystalline forms behave differently during physical processing like milling and pressing. Many process-induced solid-solid transitions of substances are known, that lead to either other crystalline forms or an amorphous form of the substance. The solid-state experts are in a constant search for crystalline forms that are chemically and physically more stable and can withstand physical stress and still retain their original properties.

Rifaximin exists in a variety of crystalline or amorphous form or a mixture of amorphous and crystalline form having distinct crystal structures and physical properties. Consequently, there is an ongoing search for a new polymorphic form of drug, which may provide improved performance thereof.

SUMMARY OF THE INVENTION

In one general aspect, there is provided a crystalline Form Z of rifaximin, which is characterized by X-ray powder diffraction pattern having characteristic peaks expressed in degrees 2θ (±0.2° 2θ) at 5.1°, 7.1°, 8.3°, and 8.6°±0.2 2θ.

In another general aspect, there is provided a crystalline Form Z of rifaximin, which is characterized by X-ray powder diffraction pattern substantially as same as depicted in FIG. 1. The polymorphic Form Z of Rifaximin is further characterized by Differential Scanning calorimetry (DSC) as shown in FIG. 2. Further, the polymorphic form Z is characterized Thermogravimetric Analysis (TGA) curve as shown in FIG. 3.

In another general aspect, there is provided a process for the preparation of novel crystalline polymorphic Form Z, the process comprising:

(a) providing a solution of rifaximin and one or more alcohol solvents at about 70° C. to 85° C.;
(b) stirring the solution for about 1 to 2 hours;
(c) cooling the solution to about 5° C. to 15° C.;
(d) seeding the solution with rifaximin form Z to obtain reaction mixture;
(e) cooling the reaction mixture to about 10° C. or below;
(f) adding water to the reaction mixture;
(g) stirring the reaction mixture for about 1 to 2 hours;
(h) filtering the reaction mixture under vacuum to obtain rifaximin form Z;
(i) suck drying the rifaximin form Z under vacuum to obtain rifaximin form Z substantially free from residual solvents; and
(j) drying under vacuum at about ambient temperature to obtain rifaximin form Z.

In another general aspect, there is provided a polymorphic Form Z of Rifaximin having purity of at least about 99% by area percentage of HPLC.

DETAILED DESCRIPTION OF THE INVENTION

The above and other objects of the present invention are achieved by the process of the present invention, which leads a process for the preparation of novel polymorphic form Z of Rifaximin.

All ranges recited herein include the endpoints, including those that recite a range "between" two values. Terms such as "about", and "generally", are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

In general, the term "substantially free from residual solvents" means residual solvents within the permissible ICH limits suitable for pharmaceutical preparations. For example but not limited to less than 0.5%, particularly less than 0.3% or more particularly less than 0.2%.

Optionally, the solution, prior to any solids formation, can be filtered to remove any undissolved solids, solid impurities prior to removal of the solvent. Any filtration system and filtration techniques known in the art can be used.

Figure 1:
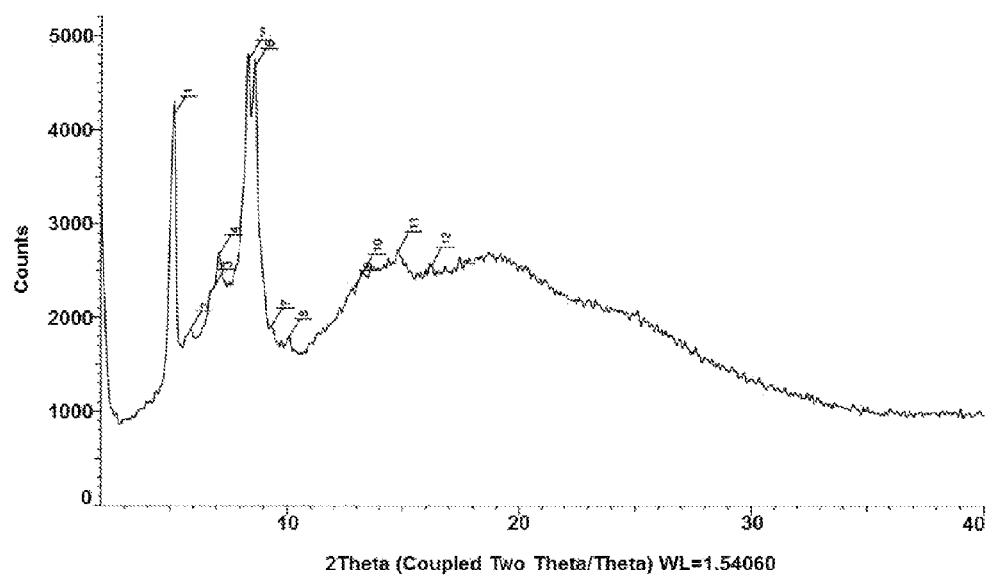
FIG. 1: X-ray powder diffraction pattern (XRD) of Rifaximin Form Z.

In one general aspect, there is provided a novel polymorphic Form Z of Rifaximin characterized by X-ray powder diffraction having characteristic peaks expressed in degrees 2θ (±0.2° 2θ) at about 5.1°, 7.1°, 8.3°, and 8.6°±0.2 2θ. The polymorphic Form Z is further characterized by X-ray powder diffraction pattern substantially as that as shown in FIG. 1.

In general, the crystalline Form. Z of rifaximin is having water content from about 4.5% to about 7.5% wt/wt.

Figure 2:
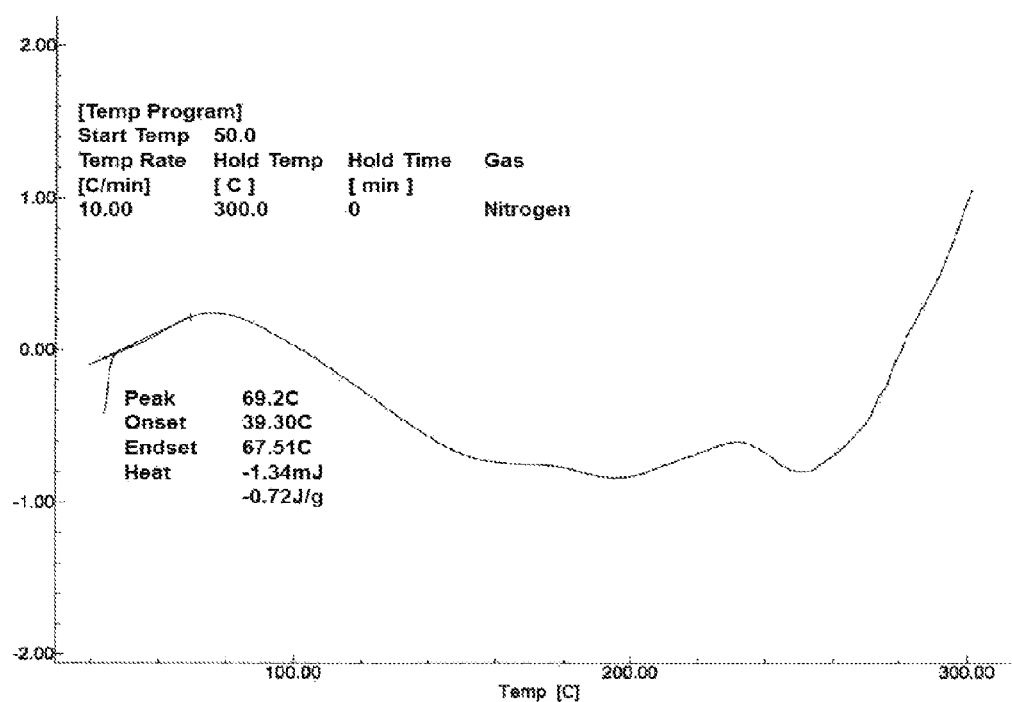
FIG. 2: Differential Scanning calorimetry (DSC) of Rifaximin Form Z.

In general, the polymorphic form Z of rifaximin is characterized by Differential Scanning Calorimetry (DSC) having onset temperature at about 39.3° C. and endothermic peak at about 69.7° C. as shown in FIG. 2.

Figure 3:
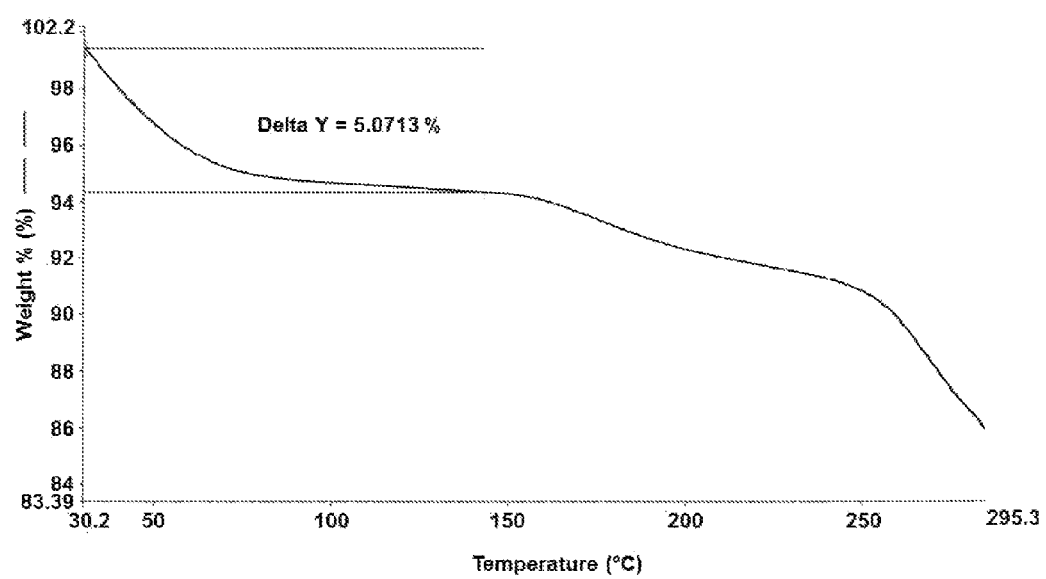
FIG. 3: Thermogravimetric Analysis (TGA) of Rifaximin Form Z.

In general, the polymorphic form Z of rifaximin is characterized by Thermogravimetric Analysis (TGA) as shown in FIG. 3.

In another general aspect, there is provided a process for the preparation of novel polymorphic form Z, the process comprising:

(a) providing a solution of rifaximin and one or more alcohol solvents at about 70° C. to 85° C.;
(b) stirring the solution for about 1 to 2 hours;
(c) cooling the solution to about 5° C. to 15° C.;
(d) seeding the solution with rifaximin form Z to obtain reaction mixture;
(e) cooling the reaction mixture to about 10° C. or below;
(f) adding water to the reaction mixture;
(g) stirring the reaction mixture for about 1 to 2 hours;
(h) filtering the reaction mixture under vacuum to obtain rifaximin form Z;
(i) suck drying the rifaximin form Z under vacuum to obtain rifaximin form Z substantially free from residual solvents; and
(j) drying under vacuum at about ambient temperature to obtain rifaximin form Z.

In general, the alcohol in step (a) comprises one or more of methanol, ethanol, propanol, isopropanol and butanol. In particular, the alcohol is ethanol.

In general, the step (a) of reaction is performed at temperature about 70° C. to 85° C. In particular, the temperature is about 75° C. to about 80° C.

In general, the step (b) of reaction is performed at temperature about 70° C. to 85° C. In particular, the temperature is about 75° C. to about 80° C. for 1 hours, particularly 1 hour.

In general, the solution was cooled in step temperature about 5° C. to 15° C. In particular, the temperature is about 10° C.

In general, the solution was cooled in step (e) at temperature about 0° C. to 10° C. In particular, the temperature is about 0° C. to 5° C.

In another general aspect, there is provided a polymorphic Form Z of Rifaximin having purity of at least about 99% by area percentage of HPLC. In particular, the polymorphic Form Z having a purity of at least about 99.5%, more particularly, a purity of at least about 99.7% by area percentage of HPLC.

In another general aspect, there is provided a polymorphic Form Z of Rifaximin with high yield of about 80% by weight. In particular, the yield is 84%, more preferably, the yield is 85% by weight.

Instrumental Details

X-ray powder diffraction (XRD) analysis was performed using Bruker Model D2 Phaser or equivalent under the following working conditions:
X-ray source: Copper Kα
Detector: LYNXEYE (1D mode)
Copper Kα-radiation: 40 kV and 40 mA
2θ range: from 2° to 40°
Step Size: 0.030
Divergent Slit: 0.300°
Antiscatter slit: 3.000 mm Approximately 150 mg sample was gently flattened on a quartz plate without further processing (e.g. Grinding and sieving) and scanned. Sample was analyzed for 10 minutes.

Differential Scanning calorimetry (DSC) analysis was performed using a differential scanning calorimeter Mettler Toledo or PerkinElmer or equivalent. The DSC cell/sample chamber was purged with 100 ml/min of ultra-high purity nitrogen. The instrument was calibrated with high purity Indium. The sample was placed into an open aluminum DSC pan and measured against an empty reference pan. About 2 mg of sample was placed into the bottom of the pan and lightly tapped down to ensure good contact with the pan. The instrument was programmed to heat at a heating rate of 10° C./min in the temperature range between 50° C. and 300° C.

Thermogravimetric Analysis (TGA) was performed using a TA instrument Mettler Toledo TGA/SDTA-851° or PerkinElmer Thermal Analysis Thermogravimetric analyzer or equivalent. Sample was placed in an aluminum sample into the TG furnace. The instrument was programmed to heat at a heating rate of 10° C./min in the temperature range between 35° C. and 300° C.

In another general aspect, there is provided a pharmaceutical composition comprising a crystalline Form Z of rifaximin and pharmaceutically acceptable carriers, excipients or diluents.

The pharmaceutical composition of the present invention may be in the form of a liquid or solid dosage forms for oral, parenteral or topical use and may have sustained or immediate release characteristics. The dosage forms possible include tablets, capsules, powders, granules, creams, injectable, solutions, elixirs or suspensions.

As used herein, the term "pharmaceutical compositions" includes pharmaceutical formulations like tablets, pills, powders, liquids, suspensions, emulsions, granules, capsules, suppositories, or injection preparations.

In general, the pharmaceutical compositions a crystalline Form Z of rifaximin of the invention may be prepared by using diluents or excipients such as fillers, bulking agents, hinders, wetting agents, disintegrating agents, surface active agents, and lubricants.

The present invention is further illustrated by the following example which is provided merely to be exemplary of the invention and do not limit the scope of the invention. Certain modification and equivalents will be apparent to those skilled in the art and are intended to be included within the scope of the present invention.

EXAMPLES

Example-1

Preparation of Polymorphic Form Z of Rifaximin

In a 250 mL four necked round bottom flask equipped with nitrogen atmosphere facility, mechanical stirrer, thermometer pocket, condenser and an addition funnel, rifaximin (12 g) and ethanol (60 mL) were charged and reaction mixture was stirred for 1 hour at 75° C. to 80° C. The reaction mixture was cooled to room temperature without external cooling. Further, the reaction mixture was cooled to 10° C. To the reaction mixture, rifaximin form Z (60 mg) was added for seeding and reaction mixture was cooled to 0° C. to 5° C. To the reaction mixture, water (60 mL) was added dropwise at 0° C. to 10° C. and then stirred for 1 hour at 0° C. to 5° C. Solid obtained was filtered under vacuum. The resulting solid was suck dried under vacuum until the ethanol content comes less than 5000 ppm. Again the resulting solid was dried under vacuum at room temperature to obtain Form Z having moisture content 5.14% wt/wt to afford 10.5 g (88%) desired compound having residual ethanol 619 ppm and purity 99.7%.

Example-2

Preparation of Polymorphic Form Z of Rifaximin

In a 2 mL four necked round bottom flask equipped with nitrogen atmosphere facility, mechanical stirrer, thermometer pocket, condenser and an addition funnel, rifaximin (120 g) and ethanol (600 mL) were charged and reaction mixture was stirred for 1 hour at 75° C. to 80° C. The reaction mixture was cooled to room temperature without external cooling. Further, the reaction mixture was cooled to 10° C. To the reaction mixture, rifaximin form Z (600 mg) was added for seeding and reaction mixture was cooled to 0° C. to 5° C. To the reaction mixture, water (600 mL) was added dropwise at 0° C. to 10° C. and then stirred for 1 hour at 0° C. to 5° C. Solid obtained was filtered under vacuum. The resulting solid was suck dried under vacuum until the ethanol content comes less than 5000 ppm. Again the resulting solid was dried under vacuum at room temperature to obtain Form Z having moisture content 5.1% wt/wt to afford 105 g (88%) desired compound having residual ethanol 1500 ppm and purity 99.7%.

While the present invention has been described in terms of its specific embodiments, certain modifications and equivalents will be apparent to those skilled in the art and are intended to be included within the scope of the present invention.

We claim:

1. A crystalline Form Z of rifaximin characterized by X-ray powder diffraction having characteristic peaks expressed in degrees 2θ (±0.2° 2θ) at about 5.1°, 7.1°, 8.3°, and 8.6°±0.2 2θ.

2. The crystalline Form Z of rifaximin according to claim 1 having water content from about 4.5% to about 7.5% wt/wt.

3. The crystalline Form Z of rifaximin according to claim 1 characterized by X-ray powder diffraction substantially as same as that depicted in FIG. 1.

4. The crystalline Form Z of rifaximin according to claim 1 characterized by differential scanning calorimetry having onset temperature at about 39.3° C. and endothermic peak at about 69.7° C.

5. A crystalline Form Z of rifaximin characterized by X-ray powder diffraction having characteristic peaks expressed in degrees 2θ (±0.2° 2θ) at about 5.1°, 7.1°, 8.3°, and 8.6°±0.2 2θ and having water content from about 4.5% to about 7.5% wt/wt.

6. A process for the preparation of crystalline Form Z of rifaximin, the process comprising:
   (a) providing a solution of rifaximin and one or more alcohol solvents at about 70° C. to 85° C.;
   (b) stirring the solution for about 1 to 2 hours;
   (c) cooling the solution to about 5° C. to 15° C.;
   (d) seeding the solution with rifaximin Form Z to obtain a reaction mixture;
   (e) cooling the reaction mixture to about 10° C. or below;
   (f) adding water to the reaction mixture;
   (g) stirring the reaction mixture for about 1 to 2 hours;
   (h) filtering the reaction mixture under vacuum to obtain rifaximin Form Z;
   (i) suck drying the rifaximin form Z under vacuum to obtain rifaximin Form Z substantially free from residual solvents; and
   (j) drying under vacuum at about ambient temperature to obtain crystalline Form Z of rifaximin.

7. The process according to claim 6, wherein alcohol in step (a) comprises one or more of methanol, ethanol, propanol, isopropanol, and butanol.

8. The process according to claim 6, wherein the crystalline Form Z of rifaximin is having a purity of at least about 99.5% by area percentage of HPLC.

9. The crystalline Form Z of rifaximin according to claim 5 substantially free from residual solvents.

10. A solid pharmaceutical composition comprising a crystalline Form Z of rifaximin and one or more pharmaceutically acceptable carriers, excipients and diluents, wherein the crystalline Form Z of rifaximin is characterized by X-ray powder diffraction having characteristic peaks expressed in degrees 2θ (±0.2° 2θ) at about 5.1°, 7.1°, 8.3°, and 8.6°±0.2 2θ and having water content from about 4.5% to about 7.5% wt/wt.

* * * * *